United States Patent [19]

Falkler

[11] Patent Number: 5,753,802
[45] Date of Patent: May 19, 1998

[54] METHODS FOR TESTING THE FOULING TENDENCY OF FCC SLURRIES

[75] Inventor: Thomas J. Falkler, Fenton, Mo.

[73] Assignee: Baker Hughes Incorporated, Houston, Tex.

[21] Appl. No.: 783,158

[22] Filed: Jan. 14, 1997

Related U.S. Application Data

[63] Continuation of Ser. No. 411,230, Mar. 16, 1995, abandoned.

[51] Int. Cl.$^6$ ................................................ G01N 33/00
[52] U.S. Cl. ................................................ 73/61.62
[58] Field of Search ................ 73/61.62, 86; 208/48 AA

[56] References Cited

U.S. PATENT DOCUMENTS

| | | | |
|---|---|---|---|
| 2,339,026 | 1/1944 | Mercer | 73/36 |
| 2,644,330 | 7/1953 | Jonach et al. | 73/61.62 |
| 3,059,467 | 10/1962 | Meguerian et al. | 73/61.62 |
| 3,148,534 | 9/1964 | Benson | 73/61.62 |
| 4,525,269 | 6/1985 | Ikematsu et al. | 208/309 |
| 4,588,178 | 5/1986 | Forester | 208/48 AA |
| 4,640,762 | 2/1987 | Woods et al. | 208/56 |
| 4,910,999 | 3/1990 | Eaton | 73/61.2 |
| 5,158,667 | 10/1992 | Barlow et al. | 208/48 AA |

*Primary Examiner*—Hezron E. Williams
*Assistant Examiner*—Jay L. Politzer
*Attorney, Agent, or Firm*—Howell & Haferkamp, LC

[57] ABSTRACT

A method for analyzing the fouling tendency of a bottoms slurry in a fluidized catalytic cracking unit, the method comprising the following steps:

(a) subjecting a sample of the bottoms slurry to a selected increased pressure above atmospheric pressure and to a selected temperature corresponding to a bottoms slurry temperature at which the bottoms slurry is proposed to be maintained in the fluidized catalytic cracking unit;

(b) maintaining the sample at the selected increased pressure and selected temperature for at least about two hours;

(c) cooling the sample and reducing the pressure;

(d) homogenizing the sample to produce a homogenized sample;

(e) extracting relatively higher molecular weight materials from the homogenized sampling and (f) analyzing the extracted relatively higher molecular weight materials for at least one equality wherein the steps (e) and (f) are carried out by:

(g) adding from about three to about five parts by weight of a solvent composition to one part by weight of a measured amount of the homogenized sample, thereby to form a liquid phase containing relatively low molecular weight slurry components and a precipitate phase containing relatively high molecular weight slurry material as a precipitate;

(h) separating out the precipitate; and (i) analyzing the precipitate for at least one quality.

23 Claims, No Drawings

5,753,802

METHODS FOR TESTING THE FOULING TENDENCY OF FCC SLURRIES

This is a continuation application of co-pending application U.S. Ser. No. 08/411,230, filed Mar. 16, 1995, now abandoned.

BACKGROUND OF THE INVENTION

1. Field of the Invention

The present invention relates to methods for carrying out fouling tests on fluidized catalytic cracking (FCC) unit bottoms slurries, and more particularly to methods for testing the fouling tendency of such slurries under simulated FCC bottoms conditions.

2. Description of the Prior Art

Fluidized catalytic cracking (FCC) is a refinery process that provides substantial economic yields. Loss of production capacity can result in thousands of dollars a day in lost profit. One of the main causes of reduced capacity is fouling. Fouling problems arise in various equipment locations, but perhaps the most frequent and significant fouling problems are those that occur in the fractionator bottoms pump-around circuit.

The path by which organic fouling proceeds is perhaps best described as a sequential process, with the key steps being polymer formation, aggregation and, finally, deposition. The polymer formation results from the temperature of the system and the olefinic nature of the FCC fractionator feed. A combination of attractive forces and chemical bonds causes aggregation between the polymers. When aggregation is allowed to proceed, a highly viscous fraction is formed in the slurry. As this fraction contacts the cooler heat exchange surfaces, the viscosity increases such that this material becomes tar-like and adheres to the surface. Some additional degradation of the adhering tars occurs, and the resulting deposit usually contains a mixture of tar-like polymers (often referred to as FCC asphaltenes), coke-like polymers and catalyst fines.

Antifoulant additive treatments of some efficacy have been employed for about ten years. However, over the years, FCC technology has been stretched to new limits, with improved catalysts, heavier feeds and more severe operating conditions, and the impact of bottoms pump-around fouling remains a costly problem.

Fouling is manifested as deposits that are formed on the metal surfaces of the processing equipment, particularly the heat exchanger in the pump-around. The deposits tend naturally to decrease the efficiency of the processing operation. The results of fouling appear in the form of heat transfer loss, pressure drop, loss in throughput rate and an increase in corrosion of the equipment. And as the fouling deposits build up on the heat exchanger in the bottoms pump-around, the effectiveness of the heat exchanger in removing heat decreases. The resulting economic penalty can be substantial, especially when unit throughput becomes constrained. Too frequently, therefore equipment and even plant shut-downs for cleaning or replacement of fouled parts are required, causing substantial economic losses.

Fouling is a major cause of another obstacle to significantly greater efficiency as well. The fractionator bottoms are slurries that are maintained at an elevated temperature, conventionally at about 650° F. to about 690° F.; that is, about 340° C. to about 365° C. The temperature is maintained by cooling the recycle stream with a heat exchanger located in the pump-around. The heat exchanger typically is run at about 400° F. (204° C.) and, as it cools the slurry, heats steam for use elsewhere in the refinery. Because conversion increases significantly with increasing temperature, it is desired to maintain the bottoms slurry as hot as possible, even in excess of 690° F. (365° C.), particularly at or above about 700° F. (about 370° C.), provided that other drawbacks in maintaining high temperatures do not offset the benefits of improved conversion.

Among the principle drawbacks of maintaining the bottoms slurry at higher temperatures is that increased temperatures increase fouling rate. Thus, some refiners decrease the fractionator bottoms temperature to reduce the effects of fouling. This practice can cause the downgrading of valuable cycle oil products to lesser-valued bottoms products, at significant financial cost. Accordingly, the tendency of bottoms slurries to foul has been a major factor not just in operating at conventional temperatures, but also in preventing the ability to achieve improved yields by operation at higher temperature.

Thus, techniques have been developed in an effort to decrease fouling, many of which involve the application of chemical additives that inhibit fouling. However, such additives inhibit the fouling to varying degrees of efficacy and variations among fouling situations mean that antifoulants suitable in one situation are unacceptable in another. Thus, an additive of ideal characteristics, including that of efficacy, and that has universal application has not been developed. Moreover, efficacy in a particular situation depends on a large number of variables making predictions impossible or at least impractical.

Therefore, a test for analyzing the fouling tendency of a particular bottoms slurry of interest under the specific conditions of concern is desired. A wait-and-see, trial-and-error approach to determine whether a particular proposed antifoulant would be suitable in the situation of concern is unacceptable. Each test can require weeks or more of trial to determine fouling tendency in an operating system and involves the dangers of failures that lead to continued fouling, of damaging equipment, of contamination of the system to be treated, of resulting shut-downs and of the need to dismantle the system to determine efficacy by inspection of the equipment. Thus, it is desirable to conduct such trials in a manner other than by subjecting the system to be treated to the experiment.

Past laboratory fouling test development has focused on simulating fouling deposition and involve the heating of the bottoms slurry according to methods in which the slurry is at a lower temperature than the test surface. For example, a heated probe is inserted into the relatively cooler slurry to cause deposition on the probe and then the fouling on the probe is measured. Methods such as the hot wire tests and pipe loops, all of which feature heated metal surfaces, are well known in the industry.

However, such methods do not seem to offer a complete explanation of the fouling process or provide a practical simulation method. And a significant reason for the inability of such methods to simulate the fractionator bottoms is that the metal surfaces of the fractionator bottoms circuit—the surfaces on which fouling deposits—are cooler than the slurry (the heat exchanger cools the slurry), while the heated probe methods employ the opposite arrangement. Such methods, therefore, have not proved satisfactory in simulating fractionation bottoms or in predicting the fouling tendency of slurries in the fractionator bottoms.

The absence of a viable laboratory test to simulate and to investigate the problem of fouling has, therefore, impeded the development of improved fouling techniques and the ability to locate and coordinate antifoulants for individual systems.

SUMMARY OF THE INVENTION

The present invention, therefore, is directed to a novel method for analyzing the fouling tendency of a bottoms slurry in a fluidized catalytic cracking unit. The method comprises several steps. First, a sample of the bottoms slurry from the fluidized catalytic cracking unit is subjected to a selected increased pressure above atmospheric pressure and to a selected temperature corresponding to a bottoms slurry temperature at which the bottoms slurry is proposed to be maintained in the fluidized catalytic cracking unit. Next, the sample is maintained at the selected increased pressure and selected temperature for at least about two hours. After that, the sample is cooled and the pressure reduced, followed by homogenization of the sample to produce a homogenized sample. Subsequently, higher molecular weight materials are extracted from the homogenized samples and those higher molecular weight materials are weighted or otherwise analyzed. Then, a solvent composition (from about three to about five parts by weight) is added to a measured amount of the homogenized sample (one part by weight), thereby to form a liquid phase containing relatively low molecular weight slurry components and a precipitate phase containing relatively high molecular weight slurry material as a precipitate. The precipitate is separated out and analyzed for at least one quality.

Among the several advantages of this invention, may be noted the provision of a method for carrying out fouling tests on FCC fractionator bottoms slurries under simulated bottoms conditions; the provision of such method that permits relatively quick analysis of the fouling tendency of the bottoms slurry in the fractionator bottoms; the provision of such method that permits measurement of fouling tendency in the fractionator bottoms under more realistic bottoms conditions; and the provision of such method that does not involve foulant deposition on heated metal surfaces.

DETAILED DESCRIPTION OF THE PREFERRED EMBODIMENTS

In accordance with the present invention, it has been discovered that subjecting a sample of the bottoms slurry to a temperature corresponding to that at which the bottoms slurry is to be maintained and to a controlled pressure for a period of at least about two hours, followed by homogenization and solvent extraction produces a precipitate that provides a good gauge of the relative fouling tendency of the bottoms slurry in the fractionator bottoms pump-around under the operating temperature, pressure, oil (slurry) composition and gas exposure of the fractionator bottoms. Thus, it has been found that it is unnecessary to induce and to measure fouling deposition. Instead, measuring the extent of aggregation resulting from this test procedure provides a good prediction of relative fouling tendency under the operating conditions.

According to the method, a sample of fractionator bottoms slurry is withdrawn from the fractionator bottoms; for example, from the pump-around. If desired, a portion of the sample may be analyzed by standard techniques for various analytical data as a reference or for a preliminary screening technique. The data may include analytical data relating to asphaltene content, solids content, API gravity, viscosity, and the like.

Next, or alternatively, the sample or portion thereof weighed and the weighed specimen added to a container. About 50 grams has been found to be a suitable sample size, although absolute specimen size is not as important as the need to know the specimen sizes for comparison between runs. The container should be a non-metallic container capable of withstanding temperatures to which it will be exposed (on the order of 700° F. (371° C.)); for example, a container made of heat-tempered glass, such as a PYREX® beaker.

The container is then placed into a temperature controlled furnace or other apparatus by which the specimen of slurry in the container can be heated and maintained at the desired temperature and pressure as to be described below. For example, the slurry specimen may be placed into a PARR® pressure vessel and the vessel closed and placed into a furnace set to a temperature corresponding to the bottoms temperature at which the fractionator bottoms is desired to be run. Ordinarily, this temperature would be in the range of about 650° F. to about 690° F. (that is, about 340° C. to about 365° C.) 685° F. (363° C.), but may, in some situations, exceed 700° F. (371° C.). In particular, in view of the ability provided by this method of testing the bottoms slurries with selected antifoulants at selected temperatures, it is believed that the ability to locate antifoulant techniques capable of preventing undue fouling at higher temperatures will be increased and the bottoms will be run at ever higher temperatures, and those high temperature conditions can be simulated in this method.

After a period sufficient for the slurry to attain the pre-selected temperature, such as about thirty minutes, the pressure may be increased to a desired level sufficient to provide reproducible pressure conditions in later comparative tests. Thus, an inert gas, such as nitrogen gas, may be added to the vessel to increase the pressure to, say, 200 psig or some other desired pressure above atmospheric. The sample is then held at the selected temperature and pressure for at least two hours, preferably at least about three hours. Generally, the specimen is maintained at the selected increased pressure and selected temperature for a period of time corresponding to at least about twice the residence time. The residence time is the time it takes for the bottoms slurry to be recycled from a point in the bottoms, through the pump-around and back to the same point in the bottoms in a residence time.

The slurry specimen may then be removed from the heat and pressure and allowed to cool for a period such as overnight. The specimen then is reheated to a temperature to fluidize the specimen. Temperatures on the order of about 100° F. (38° C.) have been found sufficient for such purposes. The specimen is homogenized, preferably by agitation such as stirring.

Next, the homogenized specimen is weighed, or a portion of the homogenized specimen is weighed. The particular amount of homogenized specimen is a matter of choice, but a useful amount of weighed specimen has been found to be about 5 grams.

A solvent composition is than added to the weighed homogenized specimen. The solvent composition and amount thereof to be added should be appropriate to separate components of the specimen. Thus, the solvent composition may be selected to selectively solubilize some of the components of the specimen, provided that enough is added to solubilize some of the components (e.g., the lighter molecular weight or less viscous materials) from the specimen, but not so much to solubilize other components (e.g., the heavier molecular weight or more viscous materials).

It has been found that only certain solvent compositions used in certain limited dosage ranges are suitable in the solubilization technique. Generally, the solvent composition should contain organic solvents and should be nonaqueous, and a mixture of heptane and pentane in a heptane to pentane weight ratio of from about 94 to about 96, preferably about 95, to 5 has been found to be suitable. And it has been found that for such solvent compositions, a solvent composition to homogenized specimen weight ratio of about 3:1 to about 5:1, such as about 4:1 to about 5:1, preferably about 4:1, is desirable. Regardless of the ratio, however, the same solvent composition and ratio should be used for all comparative tests.

The more viscous or heavier molecular weight components are then separated out. In the solubilization technique, the higher molecular weight materials are in the form of a precipitate and may be separated out by maintaining the heat on the specimen and continuing the stirring of the sample after addition of the solvent composition and then allowing the mixture to settle and cool and pouring off the liquid phase. Filtration also may be used if desired. The precipitate may be heated further to evaporate off solvent in the precipitate.

The precipitate may be then analyzed for a selected quality, particularly weight or mass, which may then be compared to that quality obtained from comparative runs on other samples.

It has been found that this technique provides excellent comparative predictions of the fouling tendencies of the particular slurries in practice in the particular fractionator bottoms. Thus, for instance, comparative runs at relatively higher and lower temperatures show relatively higher and lower fouling tendencies, respectively. The method, therefore, may be used to test the effects of various proposed antifoulants and various proposed dosages and bottoms temperatures. For example, tests, even concurrent tests, may be run without antifoulant, with various doses of antifoulant and with various doses of other antifoulants and at various temperatures. By running comparative tests, the most effective antifoulant and/or highest bottoms temperature that can be maintained without unacceptable fouling rates can be determined within a very short time and without the dangers encountered in test runs on the operating system itself.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples. In the examples, all percentages are given on a weight basis unless otherwise indicated.

EXAMPLE 1

A sample of fractionator bottoms slurry was weighed into a PYREX® beaker, which was then placed into a PARR® pressure vessel. The vessel was closed and placed into a 685° F. (363° C.) furnace (to simulate a hypothetical bottoms temperature). After about thirty minutes, when the Parr bomb and slurry sample reached the furnace temperature, nitrogen gas was added to the vessel to increase the pressure to 200 psig and the sample was held at the temperature and pressure for two hours. The vessel was then removed from the furnace and allowed to cool overnight. Upon cooling, the sample was removed from the PARR® vessel and heated to about 100° F. (38° C.) and agitated thoroughly. Next, a measured 5 gram portion of the sample was placed in a pre-weighed beaker and a dose (20 g) of a solvent mixture of heptane and pentane (95:5 by weight heptane:pentane) was added to the slurry in the beaker. The resulting mixture was stirred, heated and poured through an 11-micron filter. The insoluble material remaining in the beaker was heated for an hour at 120° F. (49° C.) to remove remaining solvent. The remaining insoluble material, the adherent residue, was weighed and found to be 0.117 grams. The same procedure was followed with another sample, except that the furnace temperature was 700° F. (371° C.) and the sample was held for two hours at that temperature. The resulting adherent residue weighed 0.143 grams. The same procedure was followed with yet another sample, except that the furnace temperature was 715° F. (379° C.) and the sample was held for two hours at that temperature. The resulting adherent residue weighed 0.191 grams. Thus, the method predicts that fouling tendency increases with increasing temperature, just as is found in practice.

EXAMPLE 2

The procedures of Example 1, above, were carried out with further fractionator bottoms slurry samples treated with chemical antifoulant. The adherent residue of the treated sample maintained at 685° F. (363° C.) weighed 6 grams. The adherent residue of the treated sample maintained at 700° F. (371° C.) weighed 0.089 grams. The adherent residue of the treated sample maintained at 715° F. (379° C.) weighed 0.116 grams. Thus, the method accurately predicted reduced fouling tendency for slurries treated with antifoulants.

In view of the above, it will be seen that the several advantages of the invention are achieved and other advantageous results attained.

As various changes could be made in the above methods and compositions without departing from the scope of the invention, it is intended that all matter contained in the above description shall be interpreted as illustrative and not in a limiting sense.

What is claimed is:

1. A method for analyzing the fouling tendency of a bottoms slurry in a fluidized catalytic cracking unit wherein the bottoms slurry is maintained approximately at a bottoms slurry temperature, the method comprising the following steps:
   (a) subjecting a sample of the bottoms slurry to a selected increased pressure above atmospheric pressure and adjusting the temperature of the sample as necessary for the sample to reach a selected temperature approximately equal to the bottoms slurry temperature;
   (b) maintaining the sample at the selected increased pressure and selected temperature for at least about two hours;
   (c) cooling the sample and reducing the pressure;
   (d) homogenizing the sample to produce a homogenized sample;
   (e) evaluating non-deposited aggregation formed within the sample, by:
      (i) extracting relatively higher molecular weight materials from the homogenized sampling and
      (ii) analyzing the extracted relatively higher molecular weight materials for at least one quality from which the fouling tendency of the bottoms slurry can be determined.

2. A method as set forth in claim 1 wherein the step (e) (i) is carried out by:

adding from about three to about five parts by weight of a solvent composition to one part by weight of a measured amount of the homogenized sample, thereby to form a liquid phase containing relatively low molecular weight slurry components and a precipitate phase containing relatively high molecular weight slurry material as a precipitate and separating out the precipitate; and wherein step (e)(ii) is carried out by: analyzing the precipitate for at least one quality.

3. A method as set forth in claim 1 wherein the sample is maintained in step (b) at the selected increased pressure and selected temperature for at least about three hours.

4. A method as set forth in claim 1 wherein the fluidized catalytic cracking unit includes a bottom with a pump-around which recycles the bottoms slurry from a point in the bottoms, through the pump-around and back to the point in the bottoms in a residence time and the sample is maintained in step (b) at the selected increased pressure and selected temperature for a period of time corresponding to at least about twice the residence time.

5. A method as set forth in claim 3 wherein the homogenization of step (d) is carried out by agitation of the sample.

6. A method as set forth in claim 2 wherein the solvent composition comprises about 94 to about 96 parts by weight heptane per five parts by weight pentane.

7. A method as set forth in claim 6 wherein the solvent composition consists essentially of about 94 to about 96 parts by weight heptane per five parts by weight pentane.

8. A method as set forth in claim 6 wherein the solvent composition is nonaqueous.

9. A method as set forth in claim 2 wherein the liquid phase is formed by adding about four to about five parts by weight of the solvent composition to one part by weight of the measured amount of the homogenized sample.

10. A method as set forth in claim 6 wherein the liquid phase is formed by adding about four to about five parts by weight of the solvent composition to one part by weight of the measured amount of the homogenized sample.

11. A method as set forth in claim 7 wherein the liquid phase is formed by adding about four to about five parts by weight of the solvent composition to one part by weight of the measured amount of the homogenized sample.

12. A method as set forth in claim 2 wherein the precipitate is separated out by pouring off the liquid phase and then heating the precipitate to evaporate off solvent in the precipitate.

13. A method as set forth in claim 2 wherein the quality for which the precipitate is analyzed is weight.

14. A method as set forth in claim 2 wherein the quality for which the precipitate is analyzed is mass.

15. A method as set forth in claim 2, further comprising, prior to step (a), the step of obtaining the sample of the bottoms slurry by withdrawal of the sample of the bottoms slurry from the fluidized catalytic cracking unit.

16. A method as set forth in claim 1 wherein the sample is held in a non-metallic container during at least steps (a) and (b).

17. A method as set forth in claim 2 wherein the fluidized catalytic cracking unit includes a bottom with a pump-around which recycles the bottoms slurry from a point in the bottoms, through the pump-around and back to the point in the bottoms in a residence time and the sample is maintained in step (b) at the selected increased pressure and selected temperature for a period of time corresponding to at least about twice the residence time.

18. A method as set forth in claim 17 wherein the solvent composition comprises about 94 to about 96 parts by weight heptane per five parts by weight pentane.

19. A method as set forth in claim 18 wherein the solvent composition consists essentially of about 94 to about 96 parts by weight heptane per five parts by weight pentane.

20. A method as set forth in claim 18 wherein the solvent composition is nonaqueous.

21. A method as set forth in claim 18 wherein the liquid phase is formed by adding about four to about five parts by weight of the solvent composition to one part by weight of the measured amount of the homogenized sample.

22. A method as set forth in claim 21 wherein the quality for which the precipitate is analyzed is weight.

analyzing the precipitate for at least one quality.

23. A method as set forth in claim 1, further comprising the step of determining the fouling tendency of the bottoms slurry from the at least one quality.

* * * * *